United States Patent [19]

Dunshee

[11] Patent Number: 5,648,166
[45] Date of Patent: Jul. 15, 1997

[54] PRESSURE-SENSITIVE ADHESIVES AND TAPE ARTICLES

[75] Inventor: Wayne K. Dunshee, Maplewood, Minn.

[73] Assignee: Minnesota Mining and Manufacturing Company, St. Paul, Minn.

[21] Appl. No.: 391,210

[22] Filed: Feb. 21, 1995

[51] Int. Cl.⁶ ........................................... B32B 7/12
[52] U.S. Cl. .................. 428/355 AC; 428/343; 524/127; 525/223
[58] Field of Search .................. 428/355, 343, 428/40.1; 524/127; 525/223

[56] References Cited

U.S. PATENT DOCUMENTS

| | | | |
|---|---|---|---|
| 3,121,021 | 2/1964 | Copeland | 117/122 |
| 4,112,177 | 9/1978 | Salditt et al. | 428/304 |
| 4,554,324 | 11/1985 | Husman et al. | 525/301 |
| 4,693,776 | 9/1987 | Krampe et al. | 156/327 |
| 4,733,659 | 3/1988 | Edenbaum et al. | 128/156 |
| 4,773,409 | 9/1988 | Cilento et al. | 128/156 |
| 4,798,201 | 1/1989 | Rawlings et al. | 128/156 |
| 4,835,217 | 5/1989 | Jorgensen et al. | 525/93 |
| 4,851,278 | 7/1989 | Enanoza | 428/195 |
| 4,871,812 | 10/1989 | Lucast et al. | 428/343 X |
| 4,952,650 | 8/1990 | Young et al. | 526/194 |
| 4,957,795 | 9/1990 | Riedel | 428/74 |
| 4,957,806 | 9/1990 | Pangrazi et al. | 428/224 |
| 5,352,516 | 10/1994 | Therriault et al. | 428/343 X |
| 5,370,924 | 12/1994 | Kochinke | 428/224 |
| 5,397,614 | 3/1995 | Patnode et al. | 428/355 X |

FOREIGN PATENT DOCUMENTS

| | | | |
|---|---|---|---|
| 454 365 A2 | 10/1991 | European Pat. Off. | |
| WO84/03837 | 10/1984 | WIPO | A61L 15/06 |
| WO93/11728 | 6/1993 | WIPO | A61F 13/58 |
| WO94/23609 | 10/1994 | WIPO | A44B 18/00 |

OTHER PUBLICATIONS

Chapter 12, "Polymer Mixtures" from *The Elements of Polymer Science and Engineering*, A. Rudin (1982).

*Primary Examiner*—Daniel Zirker
*Attorney, Agent, or Firm*—Gary L. Griswold; Walter N. Kirn; Stephen W. Bauer

[57] ABSTRACT

A pressure-sensitive adhesive composition comprising a blend of both an acrylic ester-acrylic acid-macromolecular monomer copolymer adhesive component and an acrylic ester-acrylic acid-hydroxylated ether alkyl acrylate copolymer adhesive component in a ratio range of about 90:10 to 10:90 by weight of these components, methods for making such pressure-sensitive adhesive blends and tape articles having novel pressure sensitive adhesive blend components.

9 Claims, No Drawings

PRESSURE-SENSITIVE ADHESIVES AND TAPE ARTICLES

FIELD OF THE INVENTION

The invention relates to pressure-sensitive adhesive compositions, and more particularly to pressure-sensitive adhesive compositions formed from at least two different classes of polymeric materials both of which are pressure-sensitive adhesives, methods for making such pressure-sensitive adhesives and articles having novel pressure sensitive adhesive components.

BACKGROUND OF THE INVENTION

Pressure-sensitive adhesive tapes are used for a variety of holding, protecting, sealing, masking and covering purposes. Pressure-sensitive adhesive tapes comprise a substrate and an adhesive. Pressure-sensitive adhesives generally comprise polymeric materials which adhere with a limited amount of applied force such as finger pressure and are permanently tacky.

In the medical area pressure-sensitive adhesive tapes are used for many purposes and are particularly popular for securing first aid dressings. For this use it is most desirable if the tape is compliant, adherent and non-irritating to the skin without causing damage on removal.

In order to attain the above-mentioned objectives, the pressure-sensitive adhesives useful for first aid dressings require a delicate balance of properties. It is necessary to control the viscosity and elasticity of the adhesives to provide an adhesive which initially adheres well to the skin and maintains adhesion for a selected interval without leaving a residue when removed from the skin. Further, the adhesive desirably remains non-irritating to the skin during the interval, and is compatible with various tape backings.

It is known to blend polymers to obtain various properties, however, it is difficult to obtain such blends which provide most or all of the above-mentioned desired properties. Furthermore, blends, i.e. initially homogeneous mixtures of polymers dispersed in solvents, may have a tendency to separate into non-homogeneous mixtures. This separation process is generally undesirable since it provides a mixture which lacks the desirable properties of homogeneous mixtures. It is particularly difficult to blend polymers with dissimilar properties, e.g. blending hydrophobic polymers with hydrophilic polymers is exceedingly difficult. Hydrophobic materials are by their very nature not readily mixed with hydrophilic materials. It is difficult to obtain stable blends of dissimilar polymers which do not separate even when blended in a compatible solvent. It is even more difficult to obtain a blend of dissimilar polymers which provides the desirable properties of both of the polymeric components.

Medical tapes which adhere well to moist skin over extended periods of time generally require adhesives which are substantially hydrophilic and polar in character. One such class of adhesives is described in PCT Application WO 84/03837 of Snyder and Spence (hereinafter "Snyder") entitled "Adhesive and Adhesive-Coated Sheet Material for Moist Skin" which is hereby entirely incorporated by reference. The adhesives of Snyder comprise a copolymer of copolymerized A, B and C monomers wherein A is a hydrophobic monomeric acrylic acid ester of a non-tertiary alcohol, said alcohol having from 4 to 14 carbon atoms; B is a hydrophilic monomer which has a vinyl group copolymerizable with the A monomer and is other than acrylic acid, itaconic acid, acrylamide, methacrylamide, lower alkyl-substituted acrylamide, and N-vinyl-2-pyrrolidone, the amount by weight of B monomer being about 5 to 30% of the total weight of all monomers in the copolymer; and C is at least one polar monomer copolymerizable with the A and B monomers, selected from the group consisting of acrylic acid, methacrylic acid, itaconic acid, acrylamide, methacrylamide, lower alkyl-substituted acrylamide, and N-vinyl-2-pyrrolidone, the amount by weight of C monomer being about 0.5 to 30% of the total weight of all monomers in the copolymer; wherein the A, B and C monomers are copolymerized to form a polymeric backbone and the combination of A, B and C monomers being such as to provide an adhesive-coated sheet material with an initial dry skin adhesion value of at least about 0.75 Newton per 100 millimeters of width, a dry skin adhesion value after 48 hours of not more than about 12 Newtons per 100 millimeters of width, and a moist skin adhesion value of at least about 2.2 Newtons per 100 millimeters of width. Although these adhesives include one somewhat hydrophobic comonomer, the resultant adhesives are hydrophilic.

The preferred B monomer disclosed in Snyder is a hydrophilic macromolecular monomer, and the preferred hydrophilic macromolecular monomer has the general formula X-Y-Z, wherein X is a vinyl group copolymerizable with the A monomer, Y is a divalent linking group; and Z is a monovalent polymeric moiety comprising a polyether essentially unreactive under copolymerizing conditions.

The pressure-sensitive adhesives and pressure-sensitive adhesive-coated sheet materials of the Snyder invention exhibit a balance of properties which render them particularly useful in medical and surgical applications involving adhesion to skin. These adhesives and adhesive-coated sheet materials adhere suitably to moist skin. These adhesives and adhesive-coated sheet materials further possess all of the other attributes required of a suitable adhesive or adhesive-coated sheet material for use in applications involving adhesion to normal skin. Specifically, these adhesives and adhesive-coated sheet materials exhibit suitable initial adhesion to dry skin and are removed from the skin without injury thereto or undesirable irritation thereof.

Another class of adhesives which are used as skin adhesives for medical applications are described in U.S. Pat. No. 4,693,776 of Krampe, Moore and Taylor (Krampe) entitled "Macromer Reinforced Pressure Sensitive Skin Adhesive" which is hereby entirely incorporated by reference. The adhesives of Krampe comprise a copolymer of copolymerized A, B, and C monomers wherein A is a monomeric acrylate or methacrylate ester of a non-tertiary alcohol, said alcohol having from 1 to 14 carbon atoms with the average number of carbon atoms being about 4–12; B, when used, is at least one ethylenically-unsaturated compound copolymerizable with said monomeric acrylate ester, the amount by weight of B monomer being up to 25% of the total weight of all monomers; and C is a macromer having the general formula: $X-(Y)_n-Z$ wherein X is a vinyl group copolymerizable with said A and B monomers; Y is a divalent linking group; where $n$ can be zero or 1; and Z is a monovalent polymeric moiety having a $T_g$ greater than about 20° C. and a molecular weight in the range of about 2,000 to about 30,000 and being essentially unreactive under copolymerization conditions; wherein said vinyl group and said A and B monomers form a polymeric backbone having pendant therefrom said polymeric moieties (Z) and wherein the weight of said C macromer and the inherent viscosity of the copolymer are such that the adhesive composition has a creep compliance value of at least about $1.2 \times 10^{-5}$ cm$^2$/dyne.

The skin adhesive coated sheet is preferably in the form of a tape or dressing which can be applied to skin to yield an enhanced level of initial adhesion to the skin without objectionable increase in adhesion over time.

These adhesives exhibit desirable high initial adhesion to skin, in part because of the hydrophobic nature of the macromer comonomer.

Thus, the hydrophilic adhesives of Snyder and the more hydrophobic adhesives of Krampe each provide highly desirable properties for a first aid dressing. One skilled in the art would not expect that mixtures of these adhesives would provide stable blends which would exhibit the desirable properties of both of the polymeric components. Indeed, one skilled in the art would expect that mixtures of solutions of these polymers would tend to separate into non-homogeneous mixtures of polymers.

SUMMARY OF THE INVENTION

The present invention provides pressure-sensitive adhesives. More particularly, it provides a pressure-sensitive adhesive comprising a blend of both an acrylic ester-acrylic acid-macromolecular monomer copolymer adhesive component and an acrylic ester-acrylic acid-hydroxylated ether alkyl acrylate copolymer adhesive component in a ratio range of about 90:10 to 10:90.

The present invention also provides pressure-sensitive adhesive tapes comprising a backing coated with a pressure-sensitive adhesive comprising a blend of both an acrylic ester-acrylic acid-macromolecular monomer copolymer adhesive component and an acrylic ester-acrylic acid-hydroxylated ether alkyl acrylate copolymer adhesive component in a ratio range of about 90:10 to 10:90 of these components.

The present invention further provides a process for preparing a pressure-sensitive adhesive tape comprising the steps of (1) solvent blending an acrylic ester-acrylic acid-macromolecular monomer copolymer adhesive with an acrylic ester-acrylic acid-hydroxylated ether alkyl acrylate copolymer to form a homogenous blend, (2) coating said blend onto a backing, and (3) evaporating the solvent to provide a pressure-sensitive adhesive tape.

The present invention provides an adhesive and a tape using said adhesive which combines excellent initial adhesion and persistent adhesion to moist skin. These properties are provided by the use of a surprisingly compatible blend of adhesives, which blend remains homogeneous if the blend is coated onto a backing promptly to avoid any tendency to separate into heterogeneous domains.

DETAILED DESCRIPTION OF THE INVENTION

The present invention provides novel adhesive blends with a combination of advantageous properties. These blends comprise primarily two components. The components are each described in detail followed by a description of the method of blending the two components.

First Polymeric Component

The first polymeric component increases the initial adhesion of the adhesive blend to the skin while retaining the typical advantages of acrylate ester adhesives when used as medical adhesives. The typical advantages of these adhesives include ease of manufacture, an excellent safety history and profile, high shear strength, low cost and chemical stability. This first polymeric component comprises certain copolymers, especially the A-B-C type copolymers of acrylate esters (A), ethylenically unsaturated compounds copolymerizable with acrylate esters such as acrylic and methacrylic acid (B) and macromolecular monomers (C) as described hereinafter. The acrylic esters may be esters of acrylic or methacrylic acid and are preferably acrylic acid esters. The alcohol portion of the ester is typically a non-tertiary alcohol having one to fourteen carbon atoms with the average number of carbon atoms being about four to twelve. Preferably the average number of carbon atoms is about six to ten, and most preferably about eight, for example isooctyl acrylate and ethyl(hexyl)acrylate.

The ethylenically unsaturated compounds (B monomers) copolymerizable with acrylate (and methacrylate) esters include acrylic acid, methacrylic acid, itaconic acid, acrylamide, methacrylamide, acrylonitrile, methacrylonitrile, vinyl acetate and N-vinylpyrrolidone, but acrylic acid is preferred.

The macromolecular monomers (macromers) useful as C monomers have the general formula: $X-(Y)_n-Z$ wherein X is a vinyl group copolymerizable with said A and B monomers; Y is a divalent linking group; where $n$ can be zero or 1; and Z is a monovalent polymeric moiety having a $T_g$ greater than about 20° C. and a molecular weight in the range of about 2,000 to about 30,000 and being essentially unreactive under copolymerization conditions; wherein said vinyl group and said A and B monomers form a polymeric backbone having pendant therefrom said polymeric moieties (Z) and wherein the molecular weight of said C macromer and the inherent viscosity of the copolymer are such that the adhesive composition has a creep compliance value of at least about $1.2 \times 10^{-5}$ cm$^2$/dyne. Nonlimiting examples of preferred C macromers for the purposes of the present invention are polystyrylethyl methacrylate macromers having a weight average molecular weight of about 8,000 to 15,000 g/mol. and most preferably about 10,000 g/mol. as described in Example M-3 of U.S. Pat. No. 4,693,776 and hereinafter in Example 6. These macromers are prepared by reaction of styrene with secondary-butyl lithium in cyclohexane to form "living polymers" of polystyryl lithium, "capping" with ethylene oxide followed by reaction with methacryloyl chloride to obtain a macromer of about 10,000 weight average molecular weight. Some macromers useful in the present are commercially available, e.g. polystyrylethyl methacrylate (13,000 M. wt.) is available as Chemlink® 4500 from Sartomer Chemical Company.

The amounts of A, B and C monomers in these copolymers are typically 90 percent or more by weight of A monomer and about equal amounts of B and C monomers, for example, 96 parts A monomer, 2 parts of B monomer and 2 parts of C monomer.

Second Polymeric Component

The second main component of the polymer blends of the present invention allows and enhances prolonged adhesion to skin, which is a relatively moist substrate. This component is comprised of certain copolymers of Snyder cited hereinabove as published in PCT application WO 84/03837. These copolymers include three comonomers. A first comonomer is an acrylic acid ester of a non-tertiary alcohol, said alcohol having from 4 to 14 carbon atoms. Preferably the alcohol has about 8 carbon atoms, for example isooctyl or ethylhexyl alcohol. In a preferred embodiment the alcohol is isooctyl alcohol. A second comonomer is a hydrophilic monomer which has a vinyl group copolymerizable with the acrylate ester monomer, a divalent linking group and a monovalent polyether group. The polyether group should be essentially unreactive under conditions used for forming the copolymer. Many such second comonomers are described in Snyder. These comonomers contain a plurality of hydrophilic sites such as ether groups. Preferred second comonomers are macromolecular monomers of the formula:

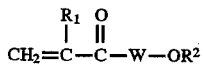 Formula III wherein $R_1$ is hydrogen or methyl, $R^2$ is hydrogen, phenyl, substituted phenyl or lower alkyl and W is a divalent poly(lower alkylene oxide) group containing 2 to 250 repeating alkoxy units and selected from the group consisting of a poly(ethylene oxide) radical, a poly(propylene oxide) radical, a radical of a copolymer of ethylene oxide and propylene oxide and a polytetrahydrofuran radical.

In a preferred embodiment the W moiety contains about 5 to 25 repeating alkoxy units, most preferably ethylenoxy units, and $R^2$ is hydrogen or lower alkyl. Such second monomers are commonly commercially available as alkoxypoly(ethylenoxy)alcohols such as methoxypolyethylenoxy)ethanols of various molecular weights. Synthesis and description of various additional suitable materials as found in Snyder is as follows:

A variety of second monomers are or have been available commercially. For example, commercially available monomers which have been found to be suitable are the 2-(2-ethoxyethoxy)ethyl acrylate available under the trade designation "SR-256" from Sartomer Company, West Chester, Pa.; the methoxy poly(ethylene oxide)$_{10}$ acrylate available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons available under the trade designations "No. 16664", "No. 16665" and "No. 16666", respectively, from Polysciences, Inc., Warrington, Pa., the hydroxy poly(ethylene oxide)$_5$ methacrylate available under the trade designation "No. 16712" from Polysciences, Inc., Warrington, Pa.

Other preferred second monomers may be prepared using commercially available starting materials and conventional methods. For example, the preferred second monomers wherein $R^2$ of Formula III is lower alkyl may be prepared by reacting an a,b-unsaturated carboxylic acid such as acrylic acid or methacrylic acid with an equimolar amount of a mono-alcohol of a poly(lower alkylene oxide). The esterification reaction is generally conducted under anhydrous conditions in an organic solvent which preferably will form an azeotropic mixture with the water which is generated as the esterification reaction proceeds. A suitable solvent is toluene. Typically, the alcohol is combined with the organic solvent and the unsaturated carboxylic acid is then added thereto. In the event that the alcohol is a solid at room temperature, it is first melted by heating prior to addition of the unsaturated carboxylic acid. The reaction is conducted in the presence of an acid catalyst such as para-toluenesulfonic acid and a free-radical inhibitor such as copper powder. The reaction mixture is refluxed, generally for 16 to 18 hours under nitrogen, and the water generated is removed, for example, using a Dean Stark trap.

Examples of suitable mono-hydroxyl-terminated poly(lower alkylene oxides) which may be used to prepare the preferred second monomers using the above-described procedure include Carbowax® 350, Carbowax® 550, Carbowax® 750, Carbowax® 2000 and Carbowax® 5000 (i.e., the methoxypoly(ethylene oxide) ethanols of about 350 MW, 550 MW, 750 MW, 2000 MW and 5000 MW, respectively, commercially available from Union Carbide Corp); a monoalcohol of a polytetrahydrofuran of about 16,000 MW prepared as described in Snyder by polymerization of tetrahydrofuran in the presence of methyl trifluoromethanesulfonate as shown in Examples for Monomer "B-9"; UCON® LB-285 (an n-butoxy poly(propylene oxide) propanol having about a 1000 MW, commercially available from Union Carbide Corp.); UCON® 50-HB260 (an n-butoxy poly(ethylene oxide/propylene oxide) (50:50 by weight) alcohol having about a 1000 MW, available from Union Carbide Corp.); and Pycal® 94 (a phenoxy poly(ethylene oxide)$_4$ ethanol, available from Atlas Chemical Industries.).

Second monomers wherein $R^2$ is hydrogen may be prepared by reacting an a,b-unsaturated carboxylic acid or hydroxyalkyl ester with an anhydride selected from monoepoxides, lactones or mixtures thereof.

The preferred second monomer for employment in preparing the pressure-sensitive adhesive copolymer is the acrylate ester of above-described Carbowax® 750.

It is to be understood that the pressure-sensitive adhesive copolymer may comprise a single type of second monomer or may comprise two or more different second monomers.

The third comonomer of the second copolymer is generally acrylic acid or methacrylic acid, preferably acrylic acid monomer.

Preparation of Polymeric Components

Either of the pressure-sensitive adhesive copolymer components of the adhesive blends of the invention may be prepared using conventional free-radical-polymerization methods. One particularly convenient method is the following. The desired amounts of each of the different monomers and an organic solvent in which the monomers are soluble are combined in a sealable bottle. A particularly suitable solvent is ethyl acetate. A solvent such as isopropyl alcohol which functions as a chain-transfer agent is also present in the reaction medium in order to control the molecular weight of the resulting adhesive copolymer. A catalytic amount of a free-radical initiator such as a,a'-azobisisobutyronitrile is then added to the solution. Nitrogen is bubbled through the solution to purge air from within the bottle, and the bottle is then sealed. The sealed bottle is tumbled in a heated water bath for a period of time sufficient to effect essentially complete polymerization. Generally, 24 hours has been found to be sufficient time to effect essentially complete polymerization when the water bath is maintained at about 55° C.

Preparation of the Adhesive Blend of the Invention

The process of blending the two copolymer components of the adhesive of the present invention to provide a useful homogeneous pressure-sensitive adhesive requires that each of the copolymer components is dissolved or dispersed in a solvent or solvent mixture. The solvents used for each of the copolymer components are preferably at least partially miscible in order to obtain good blending. Suitable solvents include esters such as ethyl acetate, dimethyl sulfoxide and N,N-dimethylformamide. Cyclohexane may be used to allow dispersions in solvent. Blending is observed visually to determine that incompatible phases are not present. It may be useful to heat one or more of the solvent mixtures to improve blending.

Once mixing of the solutions of the copolymers has provided a homogeneous blend, it is preferred to coat the adhesives onto a backing as soon as practical, but in all cases before any significant non-homogeneity of the blend is observed. Non-homogeneity would be observed e.g. by formation of heterogeneous regions (known as heterogeneous "domains"). In a preferred embodiment this coating is accomplished in about one to three hours. Nonhomogeneity is observed as soon as 0.5 hours when the blend is held at 25° C., for some blends. Therefore, coating should take place before this occurs. Each individual blend must be evaluated separately. Once the adhesive blends are coated onto backings and any remaining solvent is removed, the coatings of pressure-sensitive adhesive blend have been observed to remain stable and functional for extended periods. Preferred blends contain ratios of about 90:10 to 10:90 of the two components, but preferably 40 to 80 parts of the hydrophilic component.

Suitable backings for the pressure-sensitive adhesive of the invention comprise any of the well-known backings which find use in medical or surgical fields. Thus, the backing may be, for example, a conventional nonwoven fabric, woven fabric, knit, paper, foam, or synthetic film backing. Preferred backings are nonwoven fabrics, woven fabrics, foams, knits and the like which are breathable and which permit transpiration of perspiration and tissue or wound exudate therethrough.

The backing may be of any desired shape to provide adhesive coated sheet materials embodied as adhesive tapes, strips, wound dressings, monitoring or neuro-stimulating electrodes, drapes or the like.

The pressure-sensitive adhesive copolymer of the invention may be applied to the backing by conventional methods. As is known to those skilled in the art, the particular method selected may depend upon the nature of the backing being employed. For example, where the backing is a nonwoven fabric, a suitable method for applying the adhesive copolymer thereto involves coating a solution of the adhesive copolymer in an organic solvent onto a release liner, followed by lamination of the nonwoven fabric backing to the (semi-dry) adhesive coating.

If it is desired to improve stability of the blends by crosslinking or to sterilize the blends after coating, gamma radiation is routinely used. However, for some blends ethylene oxide is a suitable alternative for sterilization. This may be done with or without added cross-linking agents. It is preferably done without added cross-linking agents. The doses of gamma radiation used are generally 5 to 60 kilograys total dose, preferably 20 to 40 kilograys.

The following test methods were employed to evaluate the properties of articles and compositions of the invention.

Shear Creep

The Shear Creep of an adhesive is an indication of the compliance of an adhesive. Generally, adhesives having higher compliance values have increased skin adhesions.

The test method for shear creep is as follows: To measure the creep compliance of an adhesive coating, a 150-micrometer thickness of the adhesive is knife-coated onto a smooth film of polytetrafluoroethylene. The coated film is then dried to constant weight by placing it in an air-circulating oven for at least 5 minutes at 110° C. The adhesive, thus dried, is stripped from the polytetrafluoroethylene and two test pieces of equal area are die-cut and placed in a parallel-plate creep compliance rheometer, one piece being on each side of the center plate, with an outer plate contacting the exposed surface of each. Screws which connect the two outer plates are then tightened so as to compress the interposed layers of adhesive approximately 10%. The parallel plates are placed in horizontal arrangement and one end of the center plate is connected to a chart recorder. A hook is attached to the opposite end of the center plate with a flexible wire extending horizontally from the hook and then downward over a pulley, the outer plates being held in a fixed position. A suitable weight (one sufficient to measurably deform the sample a distance no greater than its thickness) is attached to the free end of the wire; then the strip chart recorder is started. The weight typically used to exert the stress on the adhesive coatings is 500 grams. From the strip chart recorder, the time and the displacement (strain) are read and the applied force (stress) is recorded. The shear creep compliance ($J_{(t)}$) at a given temperature is then calculated using the equation:

$$J_{(t)} = \frac{2AX}{hf}$$

where t is the time at which the measurement is taken, A is the area of one face of the adhesive samples, h is the thickness of the adhesive mass, X is the displacement at time t (where X is less than h) and f is the force due to the mass attached to the wire connected to the middle plate. The compliance value $J_{(t)}$ is given in cm$^2$/dyne where A is expressed in cm$^2$, h in cm, X in cm, and f in dynes.

A 1.5–2.0 compliance value for a gamma irradiated adhesive is generally preferred because adhesives having higher compliance values are too soft and demonstrate excessively high skin adhesion after 24 hours which may result in skin stripping. Additionally, adhesives having higher compliance values are soft enough to result in higher amounts of adhesive residue during wear and after removal of the adhesive. That is, adhesives with high compliance values are known to creep during wear and leave a residue on a substrate surrounding the tape or bandage backing. When removed, bandages or tapes using adhesives with high compliance values also leave adhesive residue on the substrate beneath the tape or bandage.

Skin Adhesion Procedure

A prescribed test panel of individuals is selected to embrace the normal variations in skin surface that are encountered in medical practice.

The initial skin adhesion value ($T_0$) and the skin adhesion value after 24 or 48 hours contact with the skin ($T_{24}$ or $T_{48}$) were determined using a slightly modified PSTC-1 procedure. PSTC-1 is test method No. 1 of the Pressure Sensitive Tape Council, Glenview, Ill., Seventh Edition (1976) which is hereby incorporated by reference, developed by the Specifications and Technical Committee of the Council. The test has been modified only to the extent that the tape is applied to the human skin surface on a selected area on the individual's back. The steps in the procedure are as follows:

1. Tape samples, 2.54 cm×5.09 cm, are placed on the back of the human subject.

2. Each tape is rolled down with one forward and one reverse pass, using a 1 kilogram tape roller (described in Appendix B, Sections 2.7.1, 2.8.1 and 2.8.2 of Pressure Sensitive Tape Council which is hereby incorporated by reference) moved at the rate of about 30 cm per minute.

3. Adhesion to the skin is measured as the peel force required to remove the tape at 180° angle (PSTC-1). The peel force values are measured through the use of a strain-gauge mounted on a motor-driven carriage. The force of removal is reported in grams of adhesion per 2.54 cm of width of sample. The rate of removal is 15 cm per minute.

4. The adhesion of skin is measured immediately after initial application ($T_0$) and after 24 or 48 hours of continuous contact with the skin ($T_{24}$ or $T_{48}$).

Adhesive Residue Evaluation

When the skin adhesion test described above is performed, the skin underlying the tape sample is visually inspected to determine the extent of adhesive residue left on the surface of the skin. Each sample is assigned a numerical rating from 0 to 5 based on the following scale.

| Rating | Definition |
| --- | --- |
| 0 | No visible residue |
| 1 | Only residue at edges of tape 1 |
| 2 | Residue covering 1% to 25% of tested area |
| 3 | Residue covering 25% to 50% of tested area |
| 4 | Residue covering 50% to 75% of tested area |
| 5 | Residue covering 75% to 100% of tested area |

The results of all tape samples of a given panel were averaged and are reported. Due to the subjectivity of the visual inspection of residue, no degree of precision should be inferred from the numbers to the right of the decimal point and those numbers should be treated as only rough approximations. Preferred skin adhesives will generally exhibit an average residue rating below about 2.5. A rating as high as 2.5 is acceptable if it is necessary to readhere the adhesive to skin after removal.

The following examples are provided to illustrate specific embodiments of the invention, but are not intended to be limiting thereof.

EXAMPLE 1

Preparation of a Polystyrylethyl Methacrylate Macromonomer

Preparation of Macromer

The "C" moiety of the general formula A-B-C is a polymeric material which has a copolymerizable vinyl group which copolymerizes with monomers A and B under polymerizing conditions. The C moiety, while being polymeric in one sense, actually behaves as a monomer and is referred to in the literature as a macromolecular monomer which is shortened to the term "macromer" for convenience. For the purpose of this invention, a representative preparation of the macromers that are used follows.

EXAMPLE M-1

This methacrylate-terminated styrene macromer having an average molecular weight of about 9000 was prepared using a five-liter four-necked flask, fitted with a thermometer, mechanical stirrer, septum, Dean-Stark trap and condenser. One hundred fifty grams (1.44 moles) of styrene were charged into the flask which contained 1155 grams of cyclohexane, resulting in an 11.5% by weight solution. The solution was heated to about 50° C. and a 1.4 molar solution of sec-butyl lithium in cyclohexane was added dropwise until a faint yellow color persisted, then 10.7 ml of additional sec-butyl lithium cyclohexane solution was added rapidly. The reaction mixture was maintained at 65° C. by cooling. After about one hour, the solution was allowed to cool to 35° C. and then ethylene oxide gas was introduced over the reaction mixture which was agitated rapidly for 15 minutes until the orange color of polystyryl lithium had disappeared. The reaction was then quenched with 5 ml (51.2 meq.) of methacryloyl chloride. The polymer solution was reduced in volume and the polymer precipitated, was separated and was dried. Gel permeation chromatography revealed a number average molecular weight of 8394, weight average molecular weight of 8842 and polydispersity of 1.05.

In addition to the above macromer the following macromers, prepared by means similar to that used above but increasing the amount of secondary-butyl lithium initiator, were used to prepare skin adhesives.

Example M-2: a methacrylate-terminated polystyrene macromer having a weight average molecular weight of about 10,000 g/mol.

Example M-3: a methacrylate-terminated polystyrene macromer having a weight average molecular weight of about 13,000 g/mol.

Example M-4: a methacrylate-terminated poly(methyl methacrylate) macromer having a weight average molecular weight of about 13,000 g/mol.

Example M-5: an acrylate-terminated polymethyl methacrylate polymeric monomer having an average molecular weight of 10,000 was prepared. Recrystallized dried fluorene, five parts, was placed in a 1,000 ml three-necked flask fitted with stirrer, thermometer, argon inlet and rubber septum, all of which had been previously flamed under argon. Dried tetrahydrofuran, 400 parts, was distilled into the flask and 15 parts of a 1.4N solution of sec-butyllithium in cyclohexane were added through the septum, producing an orange-red solution of "fluorenyl lithium" under slight argon pressure. The flask contents were cooled to −76° C. and 65 parts of dried, freshly distilled methyl methacrylate (MMA) were rapidly added through the septum. The reaction temperature quickly rose to −20° C. and then was gradually returned to −76° C. by cooling. After one hour of stirring, 3 parts of ethylene oxide were bubbled into the flask anti the flask was warmed to −10° C., causing the liquid to change from orange-red to light yellow. Acryloyl chloride (3 parts) was then added to quench. The reaction mixture was then warmed to room temperature and added dropwise with vigorous stirring to 4 liters of hexane, causing a white solid to precipitate. The solid was filtered, dried, redissolved in toluene, filtered to remove impurities and precipitated in methanol. The resulting white solid was a polymeric monomer having the following properties: weight average molecular weight 10,420 and polydispersity 2.6. The macromer prepared in Example M-3 was used to prepare the adhesive described in Example 2.

EXAMPLE 2

Preparation of Macromer Reinforced Pressure Sensitive Adhesive Copolymer ("Macromer Reinforced PSA")

The copolymerization reaction was carried out in a sealed, one quart bottle. A one quart (0.95 liter) glass bottle was charged with 190 grams of isooctyl acrylate, 4 grams of acrylic acid, 4 grams of 2-polystyrylethyl methacrylate macromonomer prepared according to Example M-3 in U.S. Pat. No. 4,693,776 (as prepared in Example 1), plus 300 grams of ethyl acetate, 0.6 grams of 2,2'-azobisisobutyronitrile (available from DuPont as Vazo® 64), and 2.5 grams of a 1% solution of carbon tetrabromide in isooctyl acrylate that resulted in a 0.012% by weight charge of carbon tetrabromide. The mixture was deoxygenated by purging with one liter per minute nitrogen for two minutes. The bottle was sealed and placed in a rotating water bath for twenty-four hours at 55° C. to effect essentially complete polymerization. The resulting copolymer was separated by partial evaporation of the solvent, filtration and drying, then resuspended and dissolved in ethyl acetate and was used in Example 5 to form an adhesive blend of the present invention.

EXAMPLE 3

Preparation of an Acrylate Ester of a Polyether

An acrylate ester of a polyether containing an average of about 16 repeating ethoxy units was prepared as follows.

Two hundred eighty-eight g (0.4 m) of Carbowax® 750 (a methoxy poly(ethylene oxide) ethanol of approximately 750 MW, available from Union Carbide Corp.) was melted in a 1000 ml round bottom flask fitted with a magnetic stirrer and a Dean Stark trap. Toluene, 288 g, was added to the flask and the solution was refluxed, with stirring and under a nitrogen stream, for 2 hours to remove dissolved oxygen. To this solution was then added 33.8 g (0.5 m) of acrylic acid, 9.2 g of p-toluenesulfonic acid, and 0.16 g of copper powder. The resulting mixture was then refluxed, with stirring and under a nitrogen stream, for 16 hours with generated water being collected in the Dean Stark trap. The mixture was cooled to room temperature and 10 g of calcium hydroxide was added thereto. The mixture was stirred for 2 hours and then filtered through an inorganic filtration aid. This polyether acrylate ester was then used to prepare the hydrophilic adhesive described in Example 4 below.

EXAMPLE 4

Preparation of a Hydrophilic Adhesive

The copolymerization reaction was carried out in a sealed, four ounce bottle. The bottle was charged with 21.0 grams of isooctyl acrylate, 9.54 grams of an acrylate ester of methoxy poly(ethylene oxide) ethanol of approximately 750 molecular weight in toluene at 47.16% solids prepared according to publication WO 84/03837 Example Monomer B-3 (as described in Example 3 above), 4.5 grams of acrylic acid, 0.06 grams of 2,2'-azobisisobutyronitrile (available from DuPont as Vazo® 64), 5.7 grams of isopropanol, and 19.26 grams of ethyl acetate. The mixture was deoxygenated by purging with one liter per minute nitrogen for thirty-five seconds. The bottle was sealed and placed in a rotating water bath for twenty-four hours at 55° C. to effect essentially complete polymerization. The resulting copolymer product was isolated as in Example 2 and was used in Example 5 to form an adhesive blend of the present invention.

EXAMPLE 5

Preparation of an Adhesive Blend and Adhesive Tape of the Invention

Blending Adhesive

A mixture of 887.5 g (32.1 percent by weight of the mixture) of the adhesive of Example 2 (43% solids in ethyl acetate) and 1612.5 g (67.9 percent by weight of solids) of the adhesive of Example 4 (50% solids in ethyl acetate) was blended in a roller mill blender for 96 hours to provide a solvent blend which was homogeneous to visual inspection.

Tape Preparation

The blended adhesive was coated on 50 yard (45.7 m) lengths (41.1 m for 2 mil coating gap) of a 3.5 mil (0.89 mm) thick and 12 in (30.5 cm) wide, silicone liner (available from Daubert Coated Products, Inc., Westchester, Ill. as Z-48BKF (E4-2)-8000) using a coating knife gap of either 5, 3 or 2 mils (0.102, 0.0762 and 0.0504 mm respectively) at average coating weights (2 samples) of 12.2, 7.8 and 6.5 grains per 4×6 inch sample (51, 33 and 27 grams per square meter respectively) and the solvent was evaporated in a drying oven at temperatures of 101° F. (38° C.) for Zone 1,157° F. (69° C.) for Zone 2 and 225° F. (107° C.) for Zone 3 at a line speed of about 16.5 feet per minute ($5.03^m/_{min}$).

Portions of some of the lengths of adhesive on liner were then coated with a melt blown polyurethane backing. The lengths used were each 10 yards (9.14 m), the widths used were each 12 in. (30.5 cm) and the coating weights selected were 12.2, 7.8 and 6.5 grains per 24 square inches (51, 33 and 27 grams per square meter). The polyurethane was melt blown using a process similar to the process reported in Wente, Van A., "Superfine Thermoplastic Fibers" in *Industrial Engineering Chemistry*, Vol. 48, pages 1342 et seq (1965), or in Report No. 4364 of the Naval Research Laboratories, published May 25, 1954 titled "Manufacture of Superfine Organic Fibers", by Wente, Van A., Boone, C. D. and Fluharty, E. L. both of which are hereby incorporated by reference except that the melt blowing die had smooth surface orifices (10/cm) with an 8:1 length to diameter ratio. The die temperature was maintained at 226° C., the primary air temperature and pressure were 235° C. and 150 kPa, respectively (0.76 mm gap width), and the polymer throughput rate was 131 gm/hr/cm. The resulting webs had a fiber size of 5–10 microns, basis weights and thickness of 120 g/m² and 0.305 min. and were extruded at 14 pounds per hour (6.36 kg per hour) directly onto the adhesive layer to provide a backing with a basis weight of about 120 grams per square meter. The polyurethane used for the backing was Morton PUR 440-200 (available from Morton International Inc., Chicago, Ill.) with 4 percent tan pigment (color number 1093538) available from Reed Spectrum, a division of Sandoz Chemicals Corp., Minneapolis, Minn. The tape was allowed to dry under ambient conditions.

About 4 yards (3.66 m) of tape from each roll was used for an aging study and 6 yards (5.48 m) was gamma irradiated using conventional production equipment to a total dose of about 32–35 Kilograys. Evaluation of the adhesive blend used to construct this tape by shear/creep testing is shown in Example 6. Evaluation of the tapes prepared in this Example is outlined in Example 7 with results reported in Table 2.

EXAMPLE 6

The adhesive blend from Example 5, part of which had been gamma irradiated to a total dose of about 34 Kilograys was evaluated using a rheometer for shear creep both before and after irradiation and compared to the adhesives prepared in Examples 1 and 2.

An additional adhesive was prepared from the constituent monomers instead of blending the previously prepared adhesives to prepare the adhesive designated as Adhesive Example 6 in Table 1. A copolymerization reaction was carded out in a sealed four ounce bottle. The bottle was charged with 22.35 g of isooctyl acrylate, 8.65 g of acrylate ester of methoxy poly(ethylene oxide) ethanol of approximately 750 molecular weight in toluene at 43.4% solids prepared according to publication WO 84/03837 Example Monomer B-3 (as described in Example 3 above), 3.75 g of acrylic acid 0.15 g of 2-polystyrelethyl methacrylate macromonomer prepared according to Example M-3 in U.S. Pat. No. 4,693,776 (as prepared in Example 1 above), 0.060 g of 2,2'-azobisisobutyronitrile (available) from DuPont as Vazo® 64) 4.5 g of isopropanol and 20.6 g of ethylacetate. The mixture was deoxygenated by purging with one liter per minute nitrogen for 35 seconds. The bottle was sealed and placed in a rotating water bath for 24 hours at 55 degrees C. to effect essentially complete polymerization. The resulting copolymer product was isolated as described in Example 2 above and part of the copolymer was irradiated to a total dose of about 35 kGy and tested for compliance. The compliance results are shown in Table 1 and are compared to the irradiated and nonirradiated adhesives from Examples 2 and 4 and the blended adhesive from Example 5.

TABLE 1

| Adhesive Source | Nonirradiated Compliance ($cm^2$/dyne) | Irradiated Compliance ($cm^2$/dyne) | Percent Change Compliance ($cm^2$/dyne) |
|---|---|---|---|
| Example 2 | 1.60 | 0.72 | 55.0 |
| Example 4 | 2.63 | 1.42 | 46.01 |
| Example 5 | 2.43 | 1.18 | 51.44 |
| Example 6 | 4.61 | 2.68 | 41.87 |

These results indicate that after irradiation, the compliance or the measure of adhesive firmness of the blend of Example 5 is about the same as the compliance of the adhesive of Example 4 and much better than the compliance of the adhesive of Example 2. Surprisingly, the Example 6 adhesive does not have similar compliance as the Example 5 adhesive although the amounts of the constituent macromers in each adhesive are similar. Higher compliance numbers indicate a softer adhesive which generally corresponds to increased skin adhesion.

EXAMPLE 7

Using a panel of volunteers and each of the adhesive tapes evaluated in Example 5 (having different adhesive coating weights), a comparison of the properties of (1) skin adhesion, (2) residue left on skin upon removal and (3) skin stripping were made. Micropore® adhesive tape (3M Company, St. Paul, Minn.) was used as a comparison tape in this Example. Micropore™ tape provides reliable baseline skin stripping, adhesion, and residue values for comparing with the Example tapes. The general procedure is described earlier and specifically is as follows:

Six human volunteers were selected for this panel. Subjects' backs were wiped with a 4×4 inch wet gauze pad and patted dry with a paper towel. Following the skin moistening, three sets of each bandage type were then applied to the subjects' backs and rolled with a 4½ lb. (2.0 kg) roller. All test materials were removed immediately after application to provide initial ($T_0$) skin adhesion values. Three more sets of each test material were also applied for removal after 24 hours had elapsed ($T_{24}$). Subjects were told to shower between $T_0$ and $T_{24}$ to expose the tapes to water. All did, and only with Micropore® was any edge lift detected (⅔15 is samples). At $T_{24}$ the test materials were scored for adhesive residue, skin stripping, and pain to remove as well as skin adhesion. The results are shown in Table 2.

TABLE 2

| Test Materials | Coating Weight (grains per 24 $in^2$) | Adhesion (g/in) $T_0$ | Adhesion (g/in) $T_{24}$ | Residue[1] $T_{24}$ | Skin Stripping[2] |
|---|---|---|---|---|---|
| Micropore ® Tape | — | 34 | 110 | 1.0 | 1.0 |
| Blend Adhesive Tape | 6.5 | 47 | 110 | 1.0 | 1.0 |
| Blend Adhesive Tape | 7.8 | 53 | 127 | 1.0 | 1.0 |
| Blend Adhesive Tape | 12.2 | 67 | 142 | 1.0 | 1.0 |

[1]Scored on a scale of 0–4: 0 = no lift/residue, 1 = edge/lift/residue, 2 = ≦25%, 3 = ≦50%, and 4 = ≦100%.
[2]Scored on a scale of 1–3: 1 = mild, 2 = moderate, 3 = severe.

The results in Table 2 show increasing initial adhesion to skin with increasing coating weight of the blended adhesive, with approximately twice the initial adhesion ($T_0$) for a 12 grain coating weight tape when compared to Micropore™ tape. All of the adhesives had comparable low residue and minimal skin stripping. None of the tapes were painful to remove.

EXAMPLE 8

Four different blend adhesives were prepared according to the protocol outlined in Example 5. The four adhesive blends had the following components as shown in Table 3. A fifth adhesive (8-E), the hydrophilic adhesive which is not blended, is included as a control.

TABLE 3

| Adhesive Blend | Hydrophilic Adhesive (Prepared in Example 4) | Macromer Reinforced PSA (Prepared in Example 2) |
|---|---|---|
| | Percent by weight of the dried mixture | |
| 8-A | 80 | 20 |
| 8-B | 70 | 30 |
| 8-C | 60 | 40 |
| 8-D | 50 | 50 |
| 8-E | 100 | 0 |

Adhesives 8-A, 8-B, 8-C, 8-D and 8-E were coated onto silicone liners as described in Example 5 under "Tape Preparation" using a coating knife gap of 4 mils (0.102 mm) at a coating weight of about 11 grains per 4×6 inch sample (46 $g/m^2$). Tapes were prepared and irradiated as described in Example 5 and tested for skin adhesive, residue and skin stripping as described in Example 7. Results are reported in Table 4.

TABLE 4

| Adhesive Blend | Adhesion (g/in) $T_0$ | Adhesion (g/in) $T_{24}$ | Residue $T_{24}$ | Skin Stripping[2] |
|---|---|---|---|---|
| 8-A | 29.8 | 106.0 | 0 | 0.83 |
| 8-B | 29.9 | 123.2 | 0 | 0.83 |
| 8-C | 31.5 | 127.1 | 0 | 0.89 |
| 8-D | 35.9 | 148.5 | 0 | 0.94 |
| 8-E | 28.6 | 110.0 | 0 | 0.83 |

The results demonstrate that the initial adhesion ($T_0$) and adhesion after 24 hours ($T_{24}$) increase as the amount of the Macromer Reinforced PSA increases. None of the adhesives were painful to remove. Therefore, by altering the amount of either adhesive which comprise the blend, the properties of the resulting blend adhesive vary.

What is claimed is:

1. A pressure-sensitive adhesive coating comprising a blend of A and B component adhesives wherein component A is comprised of an acrylic ester-acrylic acid-macromolecular monomer copolymer adhesive and component B is comprised of an acrylic ester-acrylic acid-hydroxylated ether alkyl acrylate copolymer adhesive and further wherein component A and component B are present in a ratio range of between about 90:10 and 10:90 by weight.

2. An adhesive according to claim 1 wherein the component ratio is between about 80:20 and 20:80 by weight component A to component B.

3. An adhesive according to claim 1 wherein the component ratio is between about 70:30 and 30:70 by weight component A to component B.

4. An adhesive according to claim 1 wherein the acrylic ester of component A is selected from six carbon to ten carbon alcohol esters of acrylic acid.

5. An adhesive according to claim 1 wherein the macromolecular monomer component is a polystyrylalkyl methacrylate or acrylate macromonomer.

6. An adhesive according to claim 5 wherein the acrylic ester of components A and B is isooctyl acrylate.

7. An adhesive according to claim 1 wherein the acrylic ester of components A and B is isooctyl acrylate.

8. A pressure-sensitive adhesive tape comprising a backing coated with a pressure-sensitive adhesive wherein the pressure-sensitive adhesive comprises a blend of A and B component adhesives wherein component A is comprised of an acrylic ester-acrylic acid-macromolecular monomer copolymer and component B is comprised of an acrylic ester-acrylic acid-hydroxylated ether alkyl acrylate copolymer.

9. The pressure-sensitive adhesive tape of claim 8 wherein the backing is comprised of a nonwoven fabric, a woven fabric, a knit fabric, a paper or a foam.

* * * * *